(12) United States Patent
Doerr et al.

(10) Patent No.: US 9,238,147 B2
(45) Date of Patent: Jan. 19, 2016

(54) CARDIAC STIMULATOR

(75) Inventors: Thomas Doerr, Berlin (DE); Ulrich Tietze, Berlin (DE)

(73) Assignee: BIOTRONIK SE & Co. KG (DE)

( * ) Notice: Subject to any disclaimer, the term of this patent is extended or adjusted under 35 U.S.C. 154(b) by 902 days.

(21) Appl. No.: 13/430,763

(22) Filed: Mar. 27, 2012

(65) Prior Publication Data

US 2012/0265085 A1 Oct. 18, 2012

Related U.S. Application Data

(60) Provisional application No. 61/475,252, filed on Apr. 14, 2011.

(51) Int. Cl.
*A61N 1/00* (2006.01)
*A61N 1/39* (2006.01)
(Continued)

(52) U.S. Cl.
CPC .............. *A61N 1/3925* (2013.01); *A61B 5/02* (2013.01); *A61B 5/04012* (2013.01); *A61N 1/0563* (2013.01); *A61N 1/3704* (2013.01)

(58) Field of Classification Search
CPC ......... A61N 1/04; A61N 1/05; A61N 1/0563; A61N 1/06; A61N 1/36; A61N 1/3605; A61N 1/36114; A61N 1/36135; A61N 1/36185; A61N 1/362; A61N 1/3621; A61N 1/38; A61N 1/385; A61N 1/39; A61N 1/3906; A61N 1/395; A61N 1/3956; A61B 5/02; A61B 5/024; A61B 5/04011; A61B 5/04012; A61B 5/0402
See application file for complete search history.

(56) References Cited

U.S. PATENT DOCUMENTS 5,658,317 A 8/1997 Haefner et al.
5,685,315 A 11/1997 McClure et al.
(Continued)

FOREIGN PATENT DOCUMENTS

EP 0 813 891 A2 12/1997
EP 1 932 563 A1 6/2008
(Continued)

OTHER PUBLICATIONS

European Search Report, EP 12 15 9236, Jul. 24, 2012, 2 pages.

*Primary Examiner* — Christopher D Koharski
*Assistant Examiner* — Elizabeth K So
(74) *Attorney, Agent, or Firm* — Craig A. Fieschko, Esq.; DeWitt Ross & Stevens S.C.

(57) ABSTRACT

An implantable cardiac stimulator includes a cardioversion/defibrillation unit connectable to at least one ventricular sensing electrode and one ventricular defibrillation electrode, and is designed to generate and deliver cardioversion or defibrillation shocks. A ventricular sensing unit having automatic threshold adaptation is connectable to the ventricular sensing electrode, and is designed to process the signals of the sensing electrode and detect a chamber contraction, and if a chamber contraction is detected, to output a ventricular sensing signal. The ventricular sensing unit processes the signals of the sensing electrode with at least two switchable sensing thresholds wherein after every sense, a VF detection window is started at a first lower sensing threshold; once the VF detection window has passed, a T wave blanking window is activated at an upper second sensing threshold; and once the T wave blanking window has passed, sensing at a second lower threshold is started.

20 Claims, 12 Drawing Sheets (51) Int. Cl.
*A61N 1/05* (2006.01)
*A61B 5/04* (2006.01)
*A61B 5/02* (2006.01)
*A61N 1/37* (2006.01)

(56) References Cited

U.S. PATENT DOCUMENTS

| | | |
|---|---|---|
| 5,891,048 A | 4/1999 | Nigam et al. |
| 6,169,918 B1 | 1/2001 | Haefner et al. |
| 7,155,282 B1 | 12/2006 | Min et al. |
| 7,181,270 B2 | 2/2007 | Breithardt et al. |
| 7,769,453 B2 | 8/2010 | Doerr et al. |
| 7,983,752 B2 | 7/2011 | Doerr et al. |
| 8,014,857 B2 | 9/2011 | Doerr |
| 8,126,540 B2 | 2/2012 | Doerr et al. |
| 2003/0074028 A1 | 4/2003 | Breithardt et al. |
| 2007/0250131 A1 | 10/2007 | Doerr et al. |
| 2007/0270911 A1 | 11/2007 | Doerr et al. |
| 2008/0147133 A1 | 6/2008 | Garner et al. |
| 2009/0125077 A1 | 5/2009 | Doerr et al. |
| 2009/0138060 A1 | 5/2009 | Doerr |
| 2009/0228057 A1 | 9/2009 | Allavatam et al. |
| 2009/0264946 A1 | 10/2009 | Doerr et al. |
| 2009/0264947 A1 | 10/2009 | Doerr et al. |
| 2009/0292330 A1 | 11/2009 | Doerr |
| 2009/0306731 A1 | 12/2009 | Doerr |
| 2009/0312812 A1 | 12/2009 | Doerr |
| 2009/0312821 A1 | 12/2009 | Doerr |
| 2010/0010607 A1 | 1/2010 | Doerr |
| 2010/0087886 A1 | 4/2010 | Busch et al. |
| 2010/0114212 A1 | 5/2010 | Doerr et al. |
| 2010/0114213 A1 | 5/2010 | Doerr |
| 2010/0114242 A1 | 5/2010 | Doerr et al. |
| 2010/0114284 A1 | 5/2010 | Doerr |
| 2010/0152550 A1 | 6/2010 | Doerr |
| 2011/0082512 A1 | 4/2011 | Doerr et al. |
| 2011/0172756 A1 | 7/2011 | Doerr et al. |
| 2012/0053507 A1 | 3/2012 | Doerr |

FOREIGN PATENT DOCUMENTS

| | | |
|---|---|---|
| WO | WO 97/06851 A1 | 2/1997 |
| WO | WO 00/24460 A1 | 5/2000 |

CARDIAC STIMULATOR

CROSS-REFERENCE TO RELATED APPLICATIONS

This application claims priority under 35 USC §119(e) to U.S. Provisional Patent Application 61/475,252 filed Apr. 14, 2011, the entirety of which is incorporated by reference herein.

FIELD OF THE INVENTION

The invention involves a device for reliably sensing ventricular fibrillation (VF) in combination with effective blanking of the T wave to prevent T wave oversensing. The invention also relates to an implantable cardiac stimulator for the treatment of tachycardiac arrhythmias.

BACKGROUND OF THE INVENTION

Tachycardia, the term referring to abnormally high heart rate, includes conditions such as tachycardiac arrhythmias, in which case an affected chamber of the heart (ventricle or atrium) contracts in an orderly manner, although at a physiologically inappropriately high rate. In the case of fibrillation, however, a heart chamber contracts in a disorderly manner due to circulating excitation, and the affected heart chamber basically no longer assists in pumping blood volume. Ventricular fibrillations (VF) can therefore be fatal. If they are detected quickly and reliably, they can be terminated using a defibrillation shock from a defibrillator.

Implantable cardiac stimulators in the form of cardiac pacemakers or implantable cardioverters/defibrillators (ICDs) are well known. Such cardiac stimulators are typically connected to electrode leads which include stimulation or defibrillation electrodes in or near a heart chamber. A cardiac pacemaker can use a stimulation electrode to deliver an electrical stimulation pulse to the muscle tissue of a heart chamber to thereby induce a stimulated contraction of the heart chamber, provided the stimulation pulse has sufficient intensity and the cardiac muscle tissue (myocardium) is not in a refractory phase at the moment. Electrode leads including stimulation electrodes having relatively small surface areas are typically used to trigger a stimulated contraction of a heart chamber in this manner, since the initial stimulation of only a small portion of the myocardium of the heart chamber is sufficient to trigger a stimulated contraction. Such a stimulated contraction of a heart chamber is referred to in this document as a "stimulated" event. If a natural contraction of the heart chamber occurs, this is referred to as a "natural" or "intrinsic" event. For example, a contraction of the right atrium of a heart may be referred to as an atrial event, which can be a natural (or intrinsic) atrial event, or where triggered by an atrial cardiac pacemaker or similar device, can be a stimulated atrial event. Similar distinctions can be made between natural (intrinsic) and stimulated left ventricular events and right ventricular events.

A local excitation of the myocardium propagates from the excitation site by conduction in the myocardium, resulting in depolarization of the muscle cells and thus contraction of the myocardium. After a short period of time the muscle cells are repolarized and the myocardium therefore relaxes. During the depolarization phase, the cardiac muscle cells are insensitive to excitation, i.e. they are refractory. The electrical potentials associated with depolarization and repolarization can be sensed, and the course thereof over time—referred to as an electrocardiogram—can be evaluated. In the electrocardiogram, a so-called R peak represents a depolarization of the ventricular myocardium and therefore a contraction of the ventricle. The repolarization of the ventricular myocardium is expressed as a so-called T wave. These signal features can be detected automatically using an appropriate sensing unit, typically by comparing signal values with threshold values. When this is done, a T wave can exceed the threshold value for detecting R peaks, and therefore a T wave is incorrectly identified as an alleged R peak. This phenomenon is referred to as T wave oversensing.

Such natural (intrinsic) events are detected by determining the electrical potentials of the myocardium of a selected heart chamber using sensing electrodes which are part of a corresponding electrode lead. The sensing electrodes can also serve as stimulation electrodes, wherein the electrodes alternate between stimulation and sensing functions (i.e., delivery and detection of potentials). Typically, a pair of electrodes composed of a tip electrode and a ring electrode is provided for the sensing, wherein the tip electrode is also used as the stimulation electrode. A bipolar recording of an intracardiac electrocardiogram (IEGM) is obtained in this manner. In that case, sensing and stimulation take place in the ventricle using a ventricular electrode lead, and stimulation and sensing take place in the (right) atrium using an atrial electrode lead which is separately connected to the cardiac stimulator. If a left ventricular electrode lead is also provided, it typically extends via the coronary sinus and a lateral vein branching off therefrom into the vicinity of the left ventricle, where it can include a stimulation electrode and/or sensing electrode having a small surface area.

During operation of the cardiac stimulator, the sensing electrodes are connected to appropriate sensing units which are designed to evaluate a recorded electrocardiogram using a sensing electrode (or a pair of sensing electrodes), and, in particular, to detect intrinsic atrial or ventricular events, i.e. natural atrial or ventricular contractions. This takes place, for example, by comparison with a threshold value, i.e. an intrinsic event is detected when a particular intracardiac electrocardiogram exceeds a suitably specified threshold value. Sensing units, which are connected to intracardiac electrodes during operation, are typically provided in an implantable cardiac stimulator for the detection of intrinsic events.

So-called blanking periods and refractory periods are typically provided during the course of sensing intrinsic events. A blanking period is started once an R peak is detected, to prevent the same event from being detected twice. No events are sensed during the blanking period. When an R peak is detected, a refractory period is also started, during which intrinsic events are sensed (outside of the blanking period), but are not detected as such. If the refractory period is dimensioned such that it extends beyond the moment when a T wave is expected, such a T wave is not detected as an intrinsic event (contraction of the heart chamber).

The intrinsic atrial heart rate (atrial frequency) or ventricular heart rate (ventricular frequency) can be derived from the frequency at which the atrial and ventricular events follow one another, thus enabling the detection of tachycardias, for example. T wave oversensing is a problem here, since T wave oversensing can suggest the alleged presence of tachycardia.

The invention assists with improving the detection of ventricular fibrillation (VF) in combination with good suppression of T wave oversensing. The solution is particularly advantageous for VF signals having significantly fluctuating amplitudes.

Input stages of modern implantable cardioverter/defibrillators (ICDs) or cardiac stimulators for cardiac resynchronization therapy (CRT-Ds) already provide algorithms for the automatic adaptation of sensing thresholds to the signal conditions. However, they typically utilize sensing thresholds that derived from measured signal amplitudes. Furthermore, to blank the T wave after detection of an R wave, a so-called upper threshold (e.g. 75% of the R wave amplitude) is often used, which is then switched to a lower threshold (e.g. 25%) after the expected duration of the T wave (e.g. after 360 ms). The result is that the T wave can be blanked in that it remains below the threshold, yet smaller fibrillation waves can then be detected using the subsequently activated lower threshold.

Typical methods have the disadvantage that fibrillation waves having greatly fluctuating amplitudes cannot be adequately sensed by using a so-called upper threshold of 75%, for example, for a period of 360 ms. However, if the upper threshold is set lower (e.g. 50%), a large T wave cannot be blanked, and so patients with large T waves are at risk of limited VF sensing.

SUMMARY OF THE INVENTION

The invention relates to an implantable cardiac stimulator, such as a cardioverter/defibrillator (ICD, CRT-D), which seeks to address the problem of combining effective T wave suppression with good VF sensing. A preferred version of the cardiac stimulator includes a sensing unit with automatic threshold adaptation which is connected (or connectable to) at least one ventricular sensing electrode and a ventricular defibrillation electrode. Signals recorded using the sensing electrodes are processed in the sensing unit with automatic threshold adaptation. The sensing unit operates using at least two switchable sensing thresholds as follows:

after every sense, a VF detection window (period) is started at a first lower sensing threshold;
  once the VF detection window has passed (i.e. the first sensing threshold was not exceeded within the VF detection window), a T wave blanking window (period) is activated at an upper second sensing threshold;
  once the T wave blanking window has passed, sensing at a second lower sensing threshold is started.

The first and second lower thresholds can be identical, and they can differ from the second sensing threshold, or the first and the second lower thresholds can differ from each other and from the second sensing threshold. Each sensing threshold represents a value which, when exceeded, triggers an event provided it occurs outside of a blanking period.

The implantable cardiac stimulator is preferably a single-chamber ICD, a dual-chamber ICD, or a three-chamber ICD.

The cardiac stimulator preferably includes a control unit which is designed to adjust the duration of the VF detection window (period) depending on the measured heart rate. Therefore the VF detection window is shortened when the heart rate is higher, and the VF detection window is extended when the heart rate is relatively lower. For example, the VF detection window can have a duration that corresponds to a defined fraction of a duration of a cardiac cycle (the reciprocal of the heart rate) measured for a specified number of previous cardiac cycles. In this manner the duration of the VF detection window can be adapted to current physiological conditions.

Preferably the duration of the VF detection window (period) is adapted as a function of a heart rate that was measured only if T wave blanking had been activated (i.e., a T wave blanking window was started) in a preceding cardiac cycle, that is, if the threshold value was not exceeded in the VF detection window within a preceding cardiac cycle.

Preferably the sensing unit is or may be connected to a sensing electrode such that intracardiac electrical potentials are detected in a bipolar manner, e.g., using two adjacent relatively small surface-area electrode poles (ring electrodes or tip electrodes) of a sensing electrode.

Alternatively, the sensing unit can also be connected or connectable to a sensing electrode such that intracardiac electrical potentials are detected in a unipolar manner, e.g., using a single relatively small surface-area electrode pole (ring electrode or tip electrode) of a sensing electrode and a relatively larger neutral pole (e.g., formed by a housing of the cardiac stimulator).

Alternatively or additionally, the sensing unit can also be connected or connectable to a sensing electrode such that it detects far-field intracardiac electrical potentials, as by using two electrode poles having a relatively large surface area, e.g. a defibrillation coil on the sensing electrode, and the housing of the cardiac stimulator as the other electrode.

Finally, the sensing unit can also be connected or connectable to several sensing electrodes such that intracardiac electrical potentials are detected using several vectors, e.g., the intracardiac potentials are detected using more than two electrode poles, wherein each vector is formed by the potential that exists between any two electrode poles.

DETAILED DESCRIPTION

Figure 1:
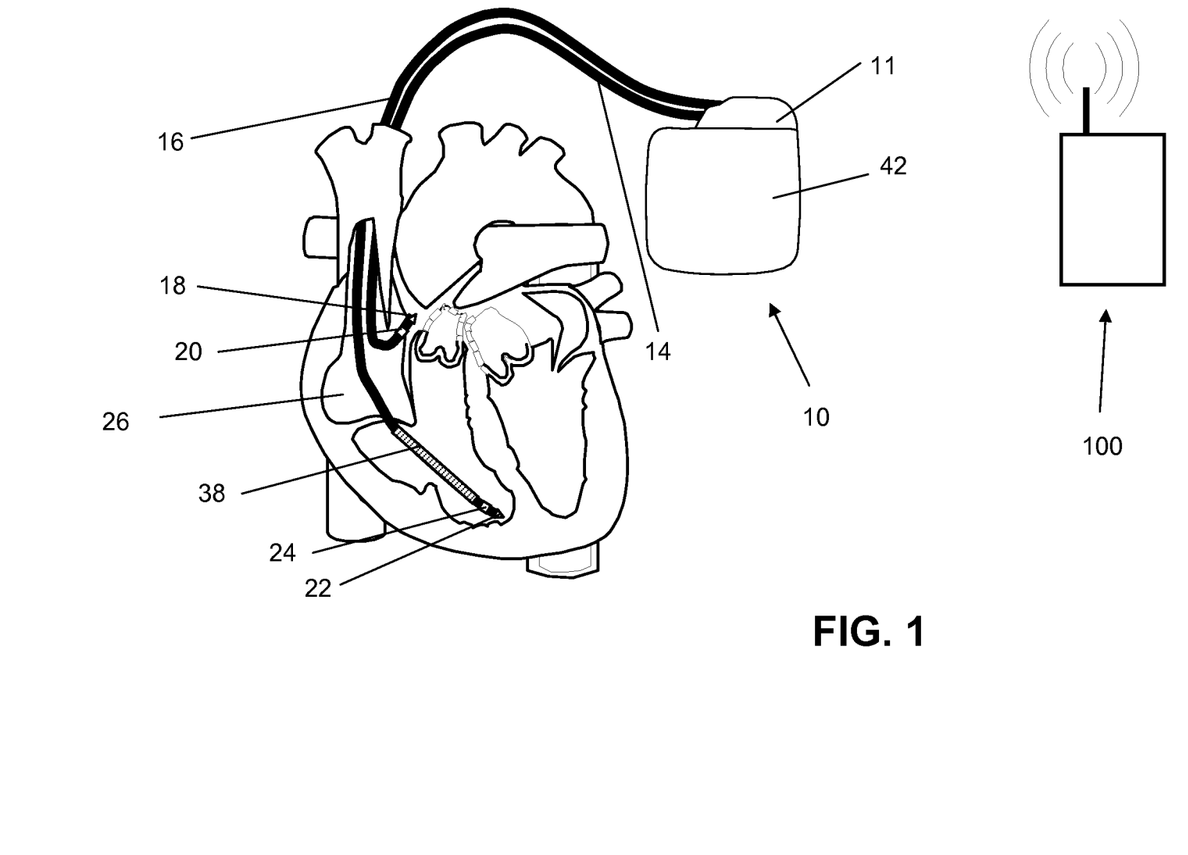
FIG. 1 schematically depicts an exemplary cardiac stimulator (a dual-chamber cardiac pacemaker and implantable cardioverter/defibrillator (ICD))

FIG. 1 shows an implantable the cardiac stimulator 10, provided in the form of a dual-chamber cardiac pacemaker and implantable cardioverter/defibrillator (ICD). The dual-chamber cardiac pacemaker 10 is connected via electrode leads 14 and 16 to stimulation and sensing electrodes 18 and 20 in the atrium, and 22 and 24 in the ventricle, and can thereby deliver stimulation pulses to, and pick up electrical potentials from, the heart. An external device 100 is also shown in the vicinity of implantable the cardiac stimulator 10.

Electrode leads 14 and 16 are electrically connected to female contacts in a header (connection housing) 11 of the cardiac stimulator 10 using conventional plug connections. In this manner, the electrode leads 14 and 16 are also connected to electronic components in the interior of a hermetically sealed metal the housing 42 of the cardiac stimulator 10. These components, which define the operation of the cardiac stimulator 10, are presented schematically in FIG. 2.

The electrode lead 14 is a right-atrial electrode lead having a distal end bearing an atrial tip electrode RA Tip 18 and a nearby atrial ring electrode RA Ring 20, both of which are located in right atrium 26 of heart 12.

The electrode lead 16 is a right-ventricular electrode lead having a distal end bearing a right-ventricular tip electrode RV Tip 22 and a nearby right-ventricular ring electrode RV Ring 24, both of which are located in the apex of the right ventricle of the heart. The right-ventricular electrode lead 16 also includes a large surface-area electrode for delivering defibrillation shocks, shown as right-ventricular shock coil RV Shock 38.

Figure 2:
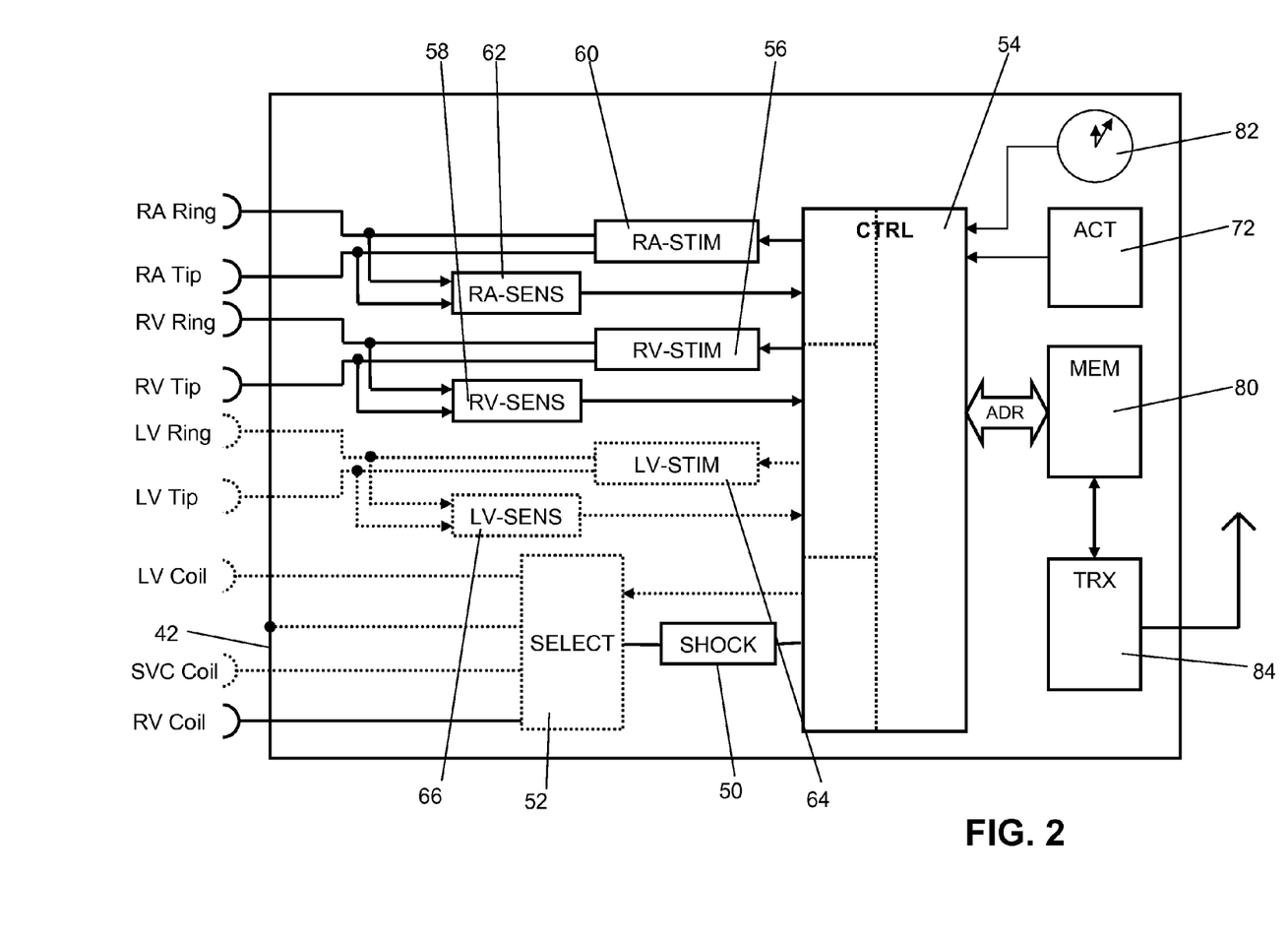
FIG. 2 provides a simplified block diagram depicting components of the exemplary dual-chamber cardiac stimulator of FIG. 1.

Some of the functional units of the cardiac stimulator 10 are depicted in FIG. 2. Components illustrated in dotted/phantom lines are those that can be additionally provided in an alternative version of the cardiac stimulator 10.

The electrical connections for the various electrodes 18, 20, 22, 24, and 38 are shown on the left side of FIG. 2. The right-ventricular shock coil RV Shock 38 is connected to a shock pulse generator 50, which is in turn connected to a the stimulation control unit 54 which triggers the shock pulse generator 50 as needed to generate and deliver a cardioversion or defibrillation shock.

The connection for the right-ventricular tip electrode RV Tip 18 and the connection for the right-ventricular ring electrode RV Ring 20 are each connected to a the right-ventricular stimulation unit 56 and a The right-ventricular sensing unit 58. The right-ventricular stimulation unit 56 and the right-ventricular sensing unit 58 are both connected to the stimulation control unit 54.

The right-ventricular stimulation unit 56 is designed to generate a right-ventricular stimulation pulse in response to a trigger signal from the stimulation control unit 54 and deliver it via the right-ventricular ring electrode RV Ring 20 and the right-ventricular tip electrode RV Tip 18. As an alternative, the housing 42 of the cardiac stimulator 10 may form a neutral electrode, and the right-ventricular stimulation unit 56 may be connected to the right-ventricular tip electrode RV Tip 18 and the housing 42 to delivering a stimulation pulse. A right-ventricular stimulation pulse differs from a defibrillation shock in that the pulse intensity of the stimulation pulse is substantially lower, and thus unlike a defibrillation shock, it does not stimulate all of the cardiac tissue (myocardium) of a ventricle at once, but only the cardiac muscle cells in the immediate vicinity of the right-ventricular tip electrode RV Tip 18. This stimulation then propagates by natural conduction across the entire ventricle, thereby stimulating contraction of the ventricle.

The right-ventricular sensing unit 58 is designed to initially amplify and filter electrical potentials present at the connection for the right-ventricular ring electrode RV Ring 20 and the right-ventricular tip electrode RV Tip 18 using an input amplifier. Furthermore, the right-ventricular sensing unit 58 is designed to evaluate the course of electrical signals present at the inputs thereof such that the right-ventricular sensing unit 58 automatically detects a natural (intrinsic) contraction of the right ventricle. This can take place, for example, by comparing the course of the signal present at the inputs of the right-ventricular sensing unit 58 with a threshold value. Typically, the greatest amplitude of the signal—the R peak—is characteristic of a natural contraction of the right ventricle, which can be detected by comparison with a threshold value.

In response, the right-ventricular sensing unit 58 provides a corresponding output signal indicating a natural contraction of the right ventricle to the stimulation control unit 54.

Analogously, the connection for the right-atrial tip electrode RA Tip 22 and the connection for the right-atrial ring electrode RA Ring 24 are connected to a right-atrial stimulation unit 60 and a right-atrial sensing unit 62 which, in turn, are connected to the stimulation control unit 54. The right-atrial stimulation unit 60 is designed to generate stimulation pulses having an intensity that is sufficient to stimulate the right-atrial myocardium. The right-atrial stimulation pulses can have a pulse intensity that differs from that of the right-ventricular stimulation pulses. The right-atrial sensing unit 62 is designed to detect a P wave, which characterizes a natural (intrinsic) contraction of the right atrium, on the basis of the course of the differential signal present at the inputs thereof. If the right-atrial sensing unit 62 detects a P wave, it generates an output signal indicating a natural contraction of the right atrium and forwards it to the stimulation control unit 54.

The cardiac stimulator 10 also includes an activity sensor 72 in connection with the stimulation control unit 54. The activity sensor 72 is designed to detect a signal which is dependent on a patient's physical activity, e.g. a motion signal, and to output a corresponding signal indicating the patient's physical activity to the stimulation control unit 54. This makes it possible for the stimulation control unit 54 to adapt the timing of the stimulation pulses to the patient's needs (hemodynamic demand).

The cardiac stimulator 10 also includes a memory unit 80 which is connected to the stimulation control unit 54 and permits it to store signals that were generated or evaluated by the stimulation control unit 54. It also enables the memory unit 80 to store control programs, in changeable form, for the stimulation control unit 54. Furthermore, the stimulation control unit 54 is connected to a timer 82.

The cardiac stimulator 10 further includes at least one bidirectional telemetry interface 84 for transmitting stored data from the stimulator 10 to an external device 100, and conversely to receive program settings and treatment commands from the external device 100.

Figure 3:
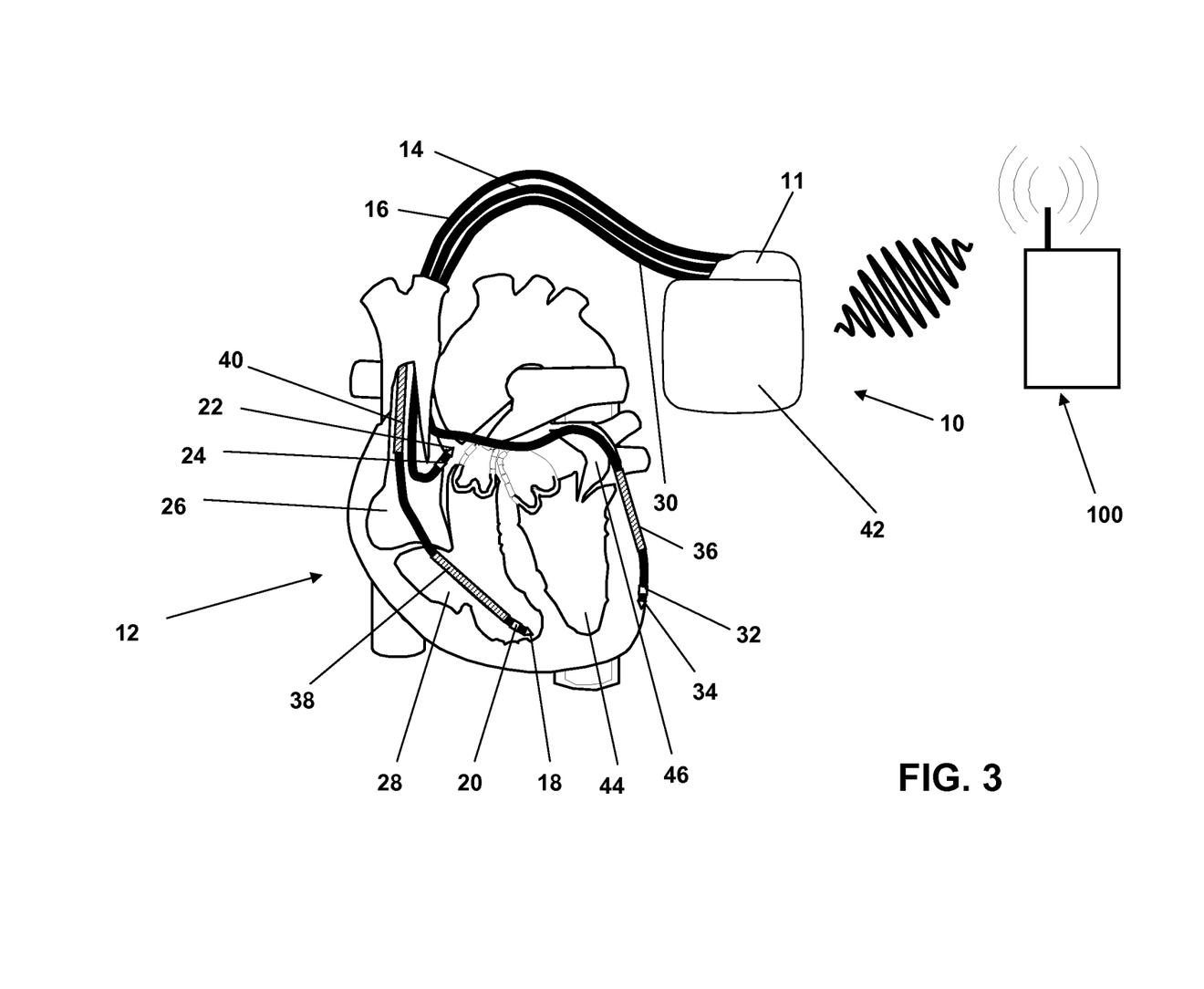
FIG. 3 schematically depicts an exemplary alternative cardiac stimulator (a three-chamber cardiac pacemaker and implantable cardioverter/defibrillator (ICD))

FIG. 3 shows an alternative version of an implantable cardiac stimulator in the form of a biventricular, three-chamber cardiac stimulator/ICD 10. It is connected via a connection block 11 (header) to a right-ventricular electrode lead 16, a right-atrial electrode lead 14, and a left-ventricular electrode lead 30, which are implanted in the heart 12. The right-ventricular electrode lead 16 includes, on the distal end thereof, a bipolar stimulation and sensing electrode with a tip electrode 18 and a ring electrode 20. The right-ventricular electrode lead 16 is further equipped with a distal shock coil 38, which is disposed in the right ventricle 28, and a proximal shock coil 40, which lies in the upper part of the right atrium 26. The atrial electrode lead 14 includes, on its distal end, a bipolar stimulation and sensing electrode composed of a tip electrode 22 and a ring electrode 24, which are implanted in the right atrium 26.

The electrode lead 30 is a left-ventricular electrode lead having a left-ventricular tip electrode LV Tip 34 and a nearby left-ventricular ring electrode LV Ring 32 at its distal end. In addition, the left-ventricular electrode lead 30 includes a left-ventricular shock coil 36 for delivering defibrillation shocks to the left ventricle 44. The left-ventricular shock coil 36 is disposed such that it extends from the left ventricle 44 upwardly to the left atrium 46. The housing 42 of the implant 10 serves as a further electrode for shock delivery.

The left-ventricular electrode lead 30 is routed out of the right atrium 26 of the heart 12 via the coronary sinus into a lateral vein branching off therefrom, and is therefore also referred to as coronary sinus electrode lead or CS electrode lead.

As shown in dotted/phantom lines in FIG. 2, the left-ventricular tip electrode LV Tip 34 and the left-ventricular ring electrode LV Ring 32 are connected to a left-ventricular stimulation unit 64 and a left-ventricular sensing unit 66. The left-ventricular stimulation unit 64 and the left-ventricular sensing unit 66 are likewise connected to the stimulation unit 54. Both of them function in a manner similar to that of the above-described stimulation units 56 and 60 and the sensing units 58 and 62. The left-ventricular shock coil 36 is likewise connected to the shock generator 50 via a connection LV-COIL and an electrode selection unit 52. Using the electrode selection unit 52, the control unit 54 can select two or more electrodes (including the conductive housing 42) to deliver a shock.

Figure 4:
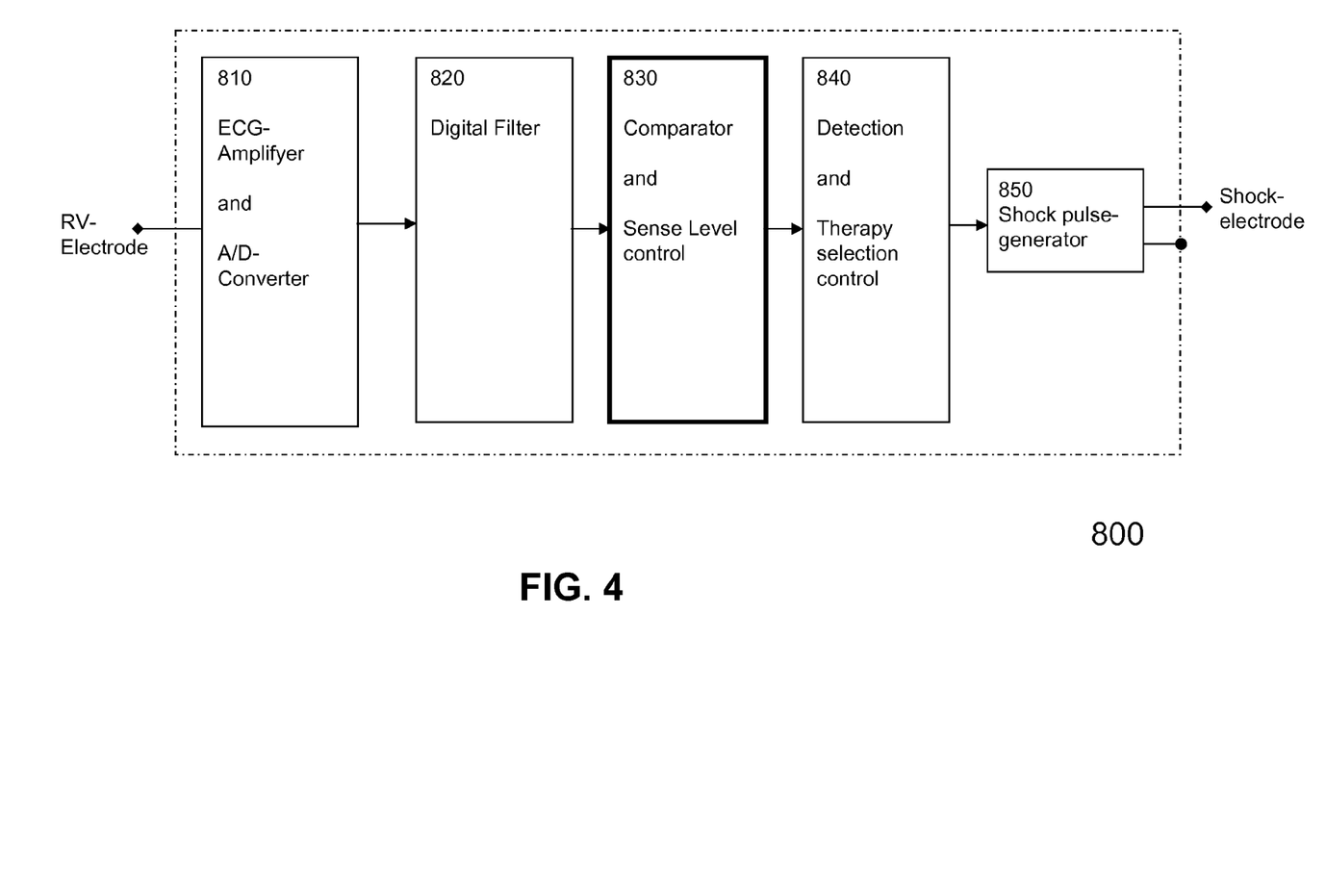
FIG. 4 shows a section of a block diagram of a dual-chamber ICD (such as that of FIG. 1) with a VF detection window (period)

FIG. 4 shows a block diagram of a ventricular fibrillation (VF) detection system, which is defined as a section of the dual-chamber ICD block diagram of FIG. 2. The right-ventricular electrode (RV), e.g., electrode 16 of FIG. 1, is connected to an EKG amplifier and an analog-to-digital converter unit 810. The digitized intracardiac electrocardiogram (IEGM) signal is then filtered at digital filter 820 and transmitted to a comparator unit 830, which determines ventricular sensing events by using threshold adaptation, including the VF detection window/period described above (and below). The ventricular sensing signals are then evaluated in a detection and therapy control unit 840, and antitachycardial therapy, e.g. defibrillation from shock generator 850, is delivered if necessary.

Figure 5:
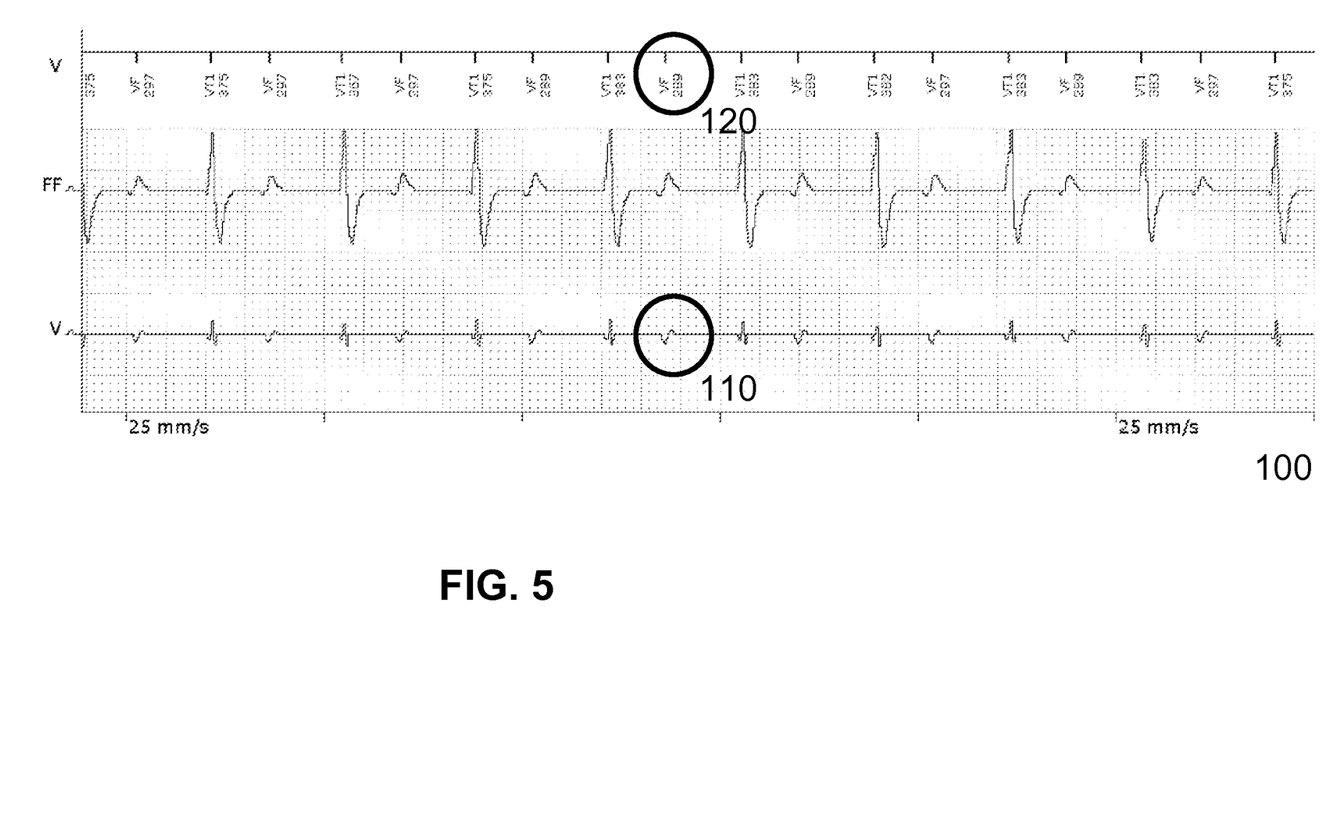
FIG. 5 shows an example of T wave oversensing.

FIG. 5 shows a typical example of T wave oversensing. T waves 110 that are pronounced in the ventricular IEGM morphology are visible in the recorded EKG and marker strips 100; the amplitude thereof is greater than 50% of the preceding R wave amplitudes. In the standard setting, this results in inadequate sensing of the T waves 120 and a resulting misinterpretation of the rhythm as ventricular fibrillation (VF). The consequence of this oversensing can be inadequate shock deliveries by the ICD.

Figure 6:
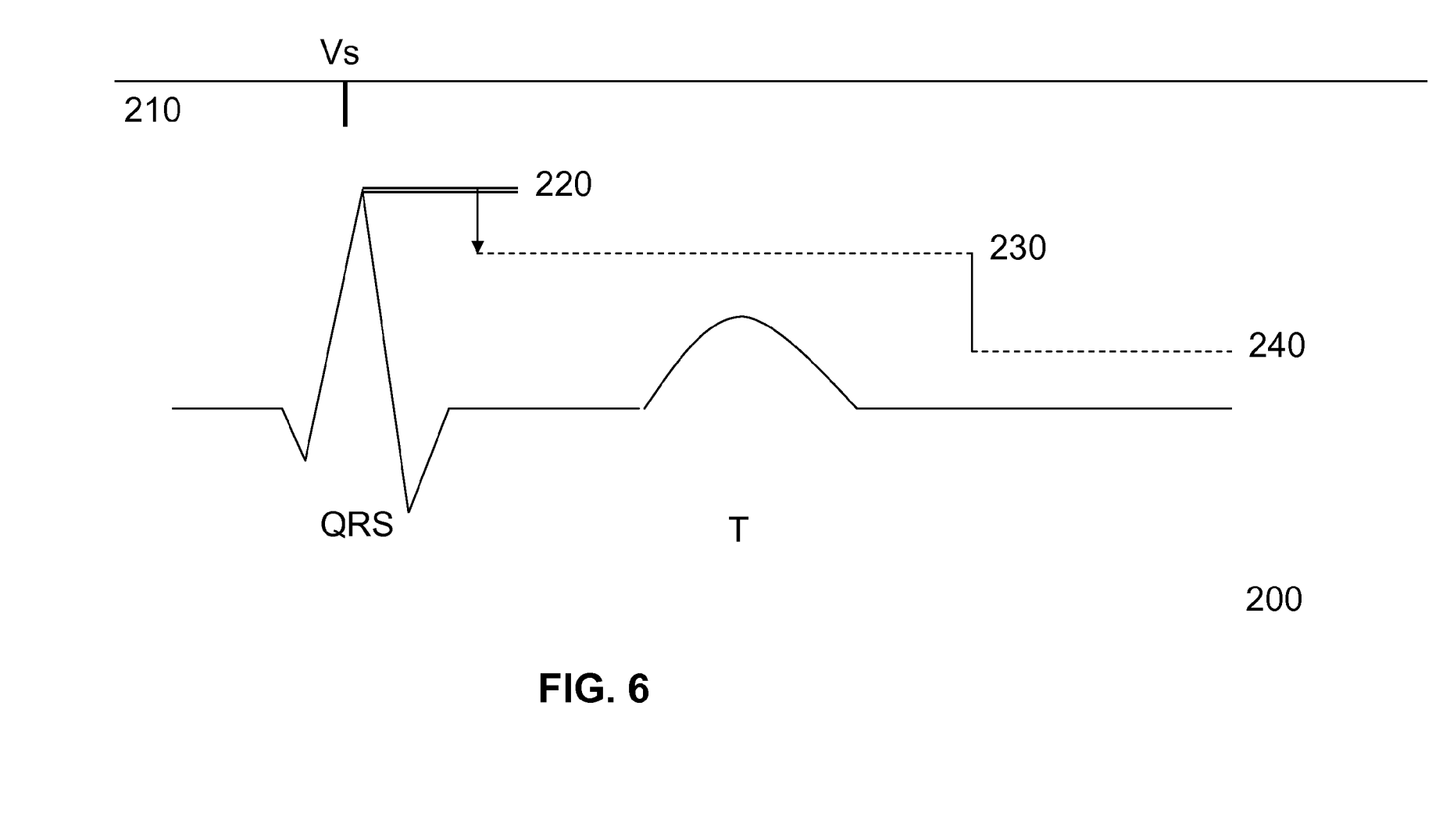
FIG. 6 shows an example of T wave suppression without a VF detection window (period)

A prior arrangement is depicted in FIG. 6. To prevent the T wave oversensing shown in FIG. 5, the sensing thresholds for an ICD system may be switched in 2 stages. In this case, after every ventricular sensing Vs (in marker channel 210), the maximum value of IEGM signal amplitude 220 is determined and, on the basis thereof, a so-called upper sensing threshold 230 is derived and activated. This threshold can be set as a percentage of the maximum value; to prevent the T wave oversensing illustrated in FIG. 1, it could be, for example, 75%, and could remain activated until the T wave has died out (e.g., at 360 ms). Afterward, a so-called lower threshold 240 is activated, which is typically 25% of the maximum IEGM signal amplitude 220. This lower threshold 240 makes it possible to sense ventricular fibrillary signals having a much smaller signal amplitude than the regular R wave (QRS).

Figure 7:
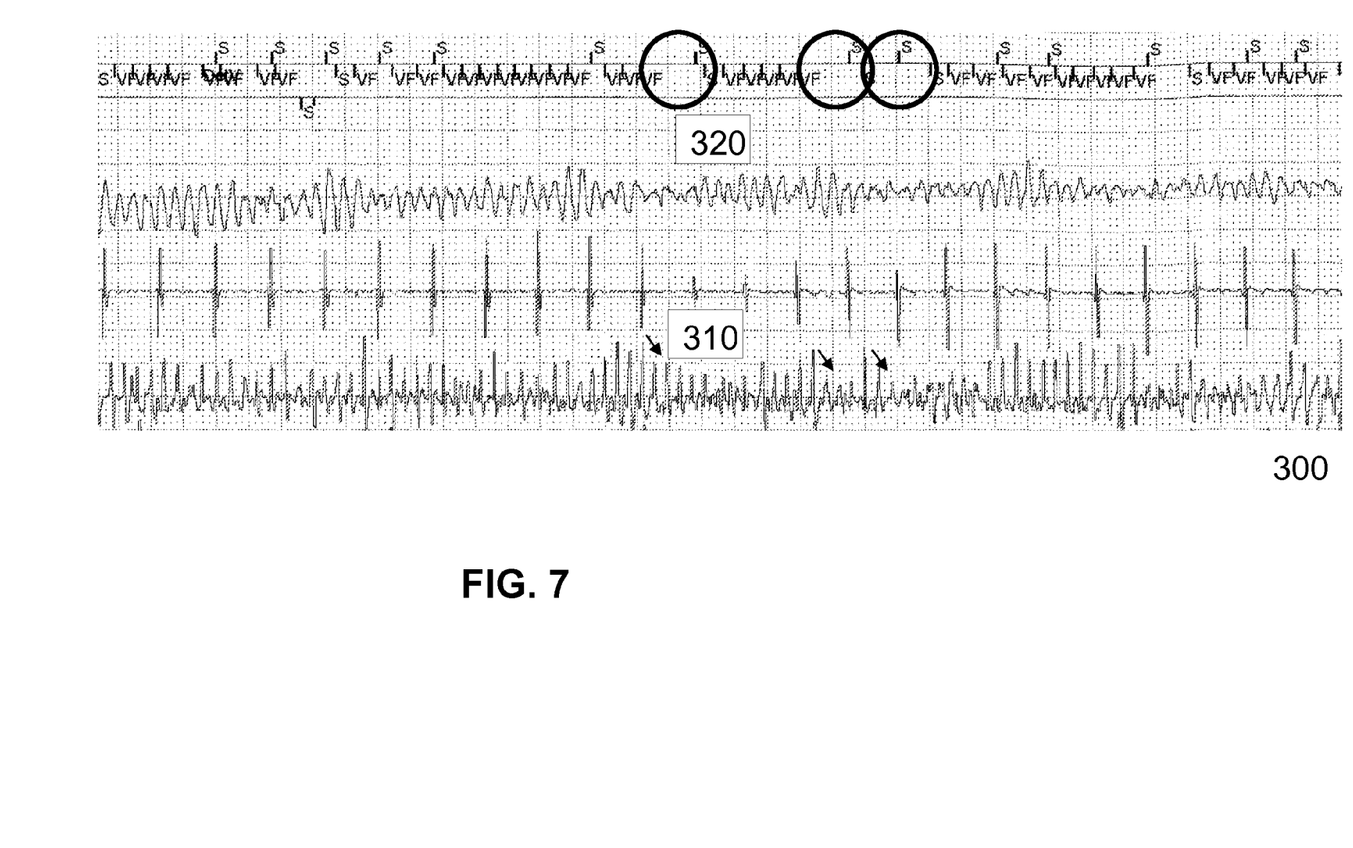
FIG. 7 shows an example of VF undersensing without a VF detection window (period)

FIG. 7 then illustrates the disadvantage of increased T wave suppression with an upper threshold of 75%. The depicted IEGM recording 300 exhibits VF signal amplitudes (see arrow near reference numeral 310) in the ventricular channel that clearly fluctuate by more than 25%. Due to the elevated upper threshold, this often results in sensing failures (undersensing) in the ventricular marker channel (top diagram 320), and therefore results in delayed detection of ventricular fibrillation.

Figure 8:
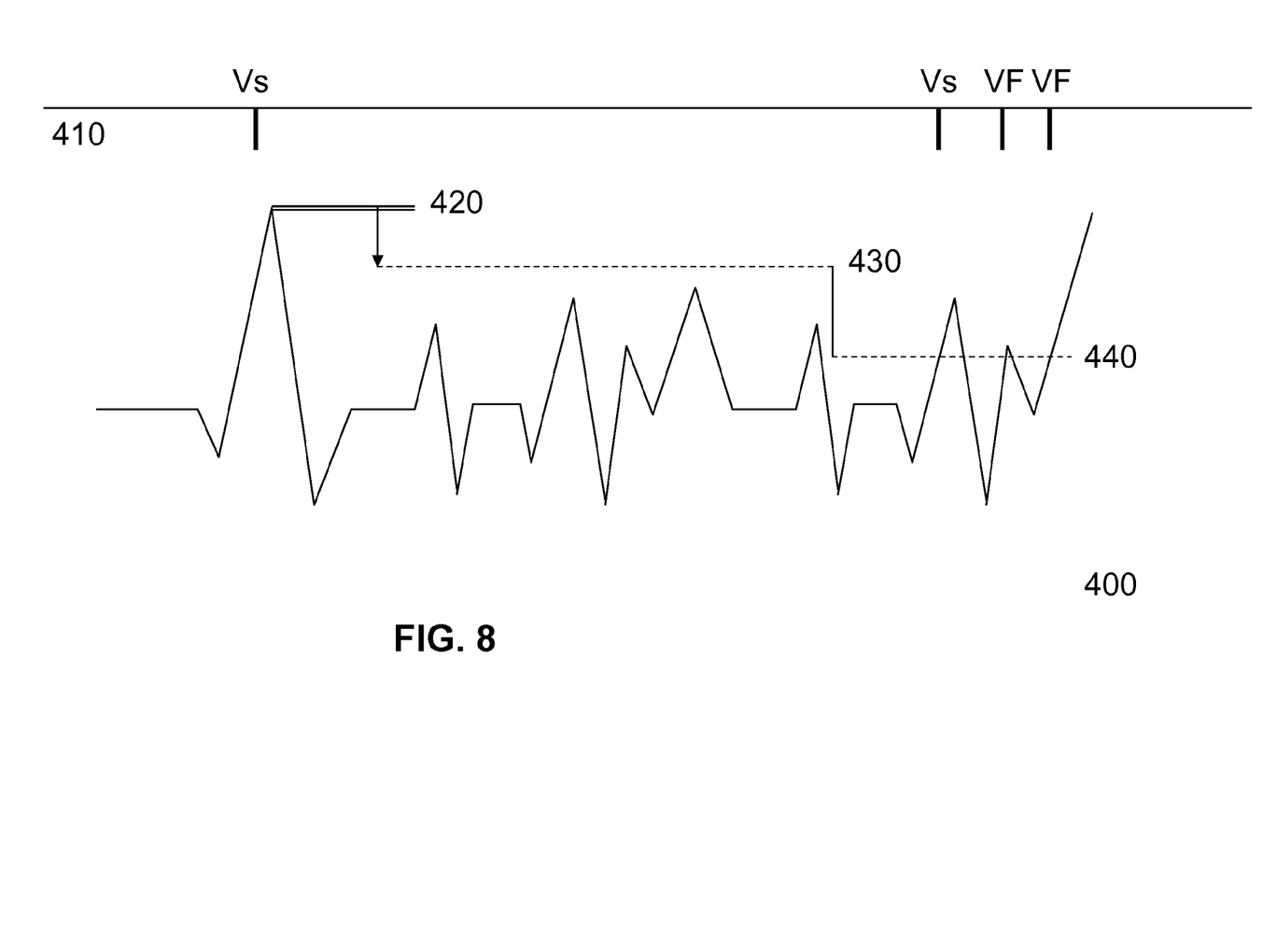
FIG. 8 shows an example of VF detection without a VF detection window (period)

FIG. 8 is another illustration of the mechanism of VF undersensing using an excessively high upper threshold 430 of 75% of IEGM maximum value 420. Fibrillation with fluctuating (but relatively great) amplitude sets in after sensing takes place, and is initially not detected since all of the signals lie below an upper threshold 430. The fibrillary signals are finally sensed and depicted accordingly in the marker channel (upper diagram 410) after switching to a lower threshold 440. The first marker is labeled as Vs, however, due to the excessive distance from the previous marker, thereby delaying the VF detection. The situation can repeat itself several times if signal amplitudes fluctuate frequently during fibrillation.

Figure 9:
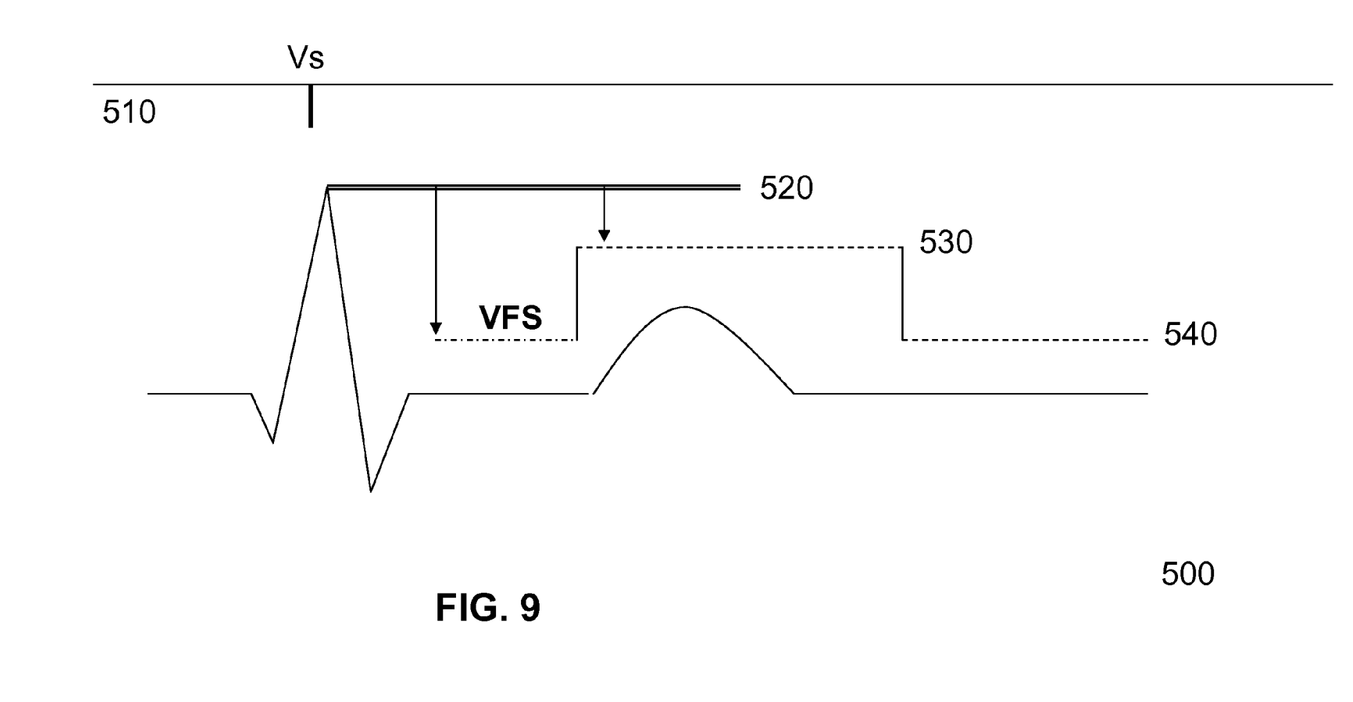
FIG. 9 shows an example of T wave suppression with a VF detection window (period)

FIG. 9 shows the additional VF detection window (period) VFS according to the invention, which begins after a ventricular sensing Vs. Lower threshold 540, or a threshold that is much lower than upper threshold 520, is active within the VF detection window VFS. The T wave is blanked as usual via upper threshold 530 which is started after the VF detection window VFS. The duration of the VF detection window VFS is dimensioned such that a T wave should not be expected within the VF detection window VFS, e.g., the VF detection window VFS ends between 150 ms and 250 ms after a ventricular sensing Vs occurs. Optionally, the duration of the VF detection window VFS can be dependent on the heart rate, and can be shortened at higher heart rates. Lower threshold 540 is activated at the end of the T wave blanking period 530, as is typical.

Figure 10:
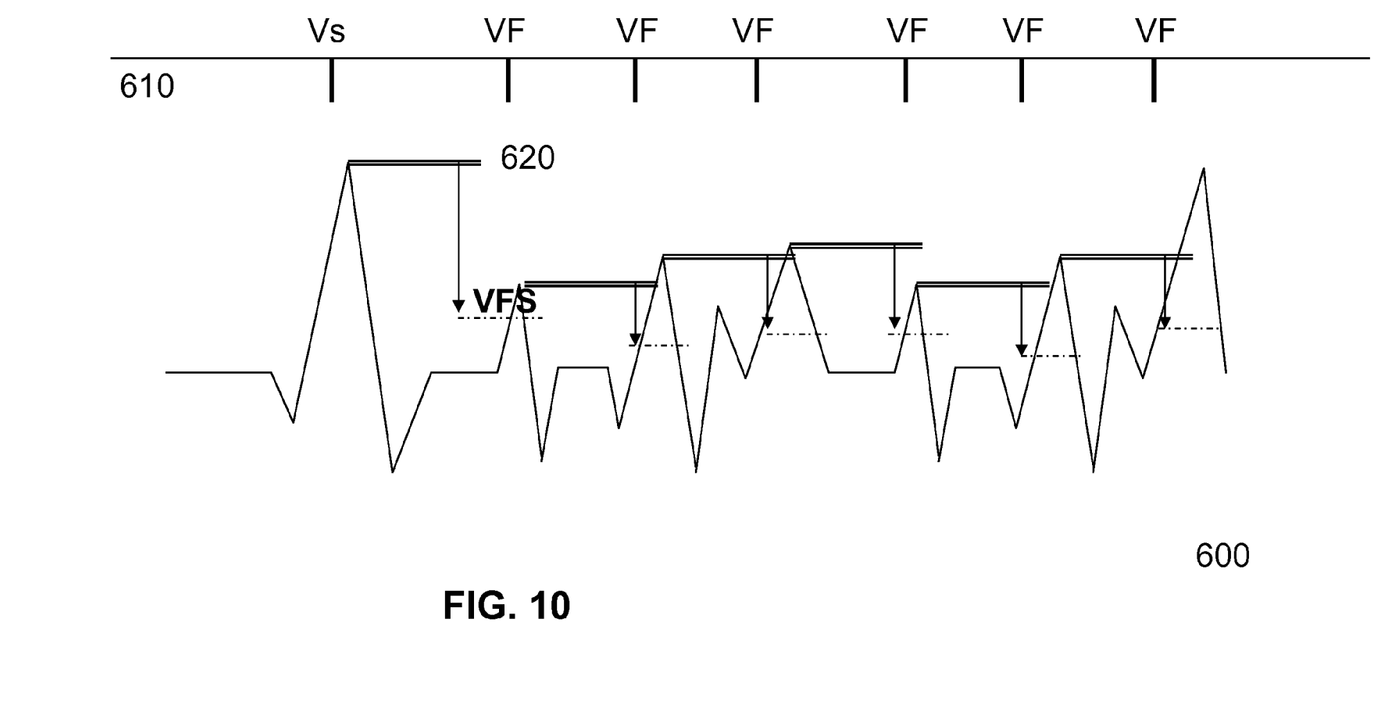
FIG. 10 shows an example of VF detection with a VF detection window (period)

FIG. 10 shows the efficacy of the VF detection window (period) VFS in the case of ventricular fibrillation (VF). The fibrillary signals are reliably labeled as VF in marker channel 610 despite greatly fluctuating amplitudes, since the VF detection window VFS is restarted with every ventricular sensing Vs, and therefore the upper threshold is not activated.

Figure 11:
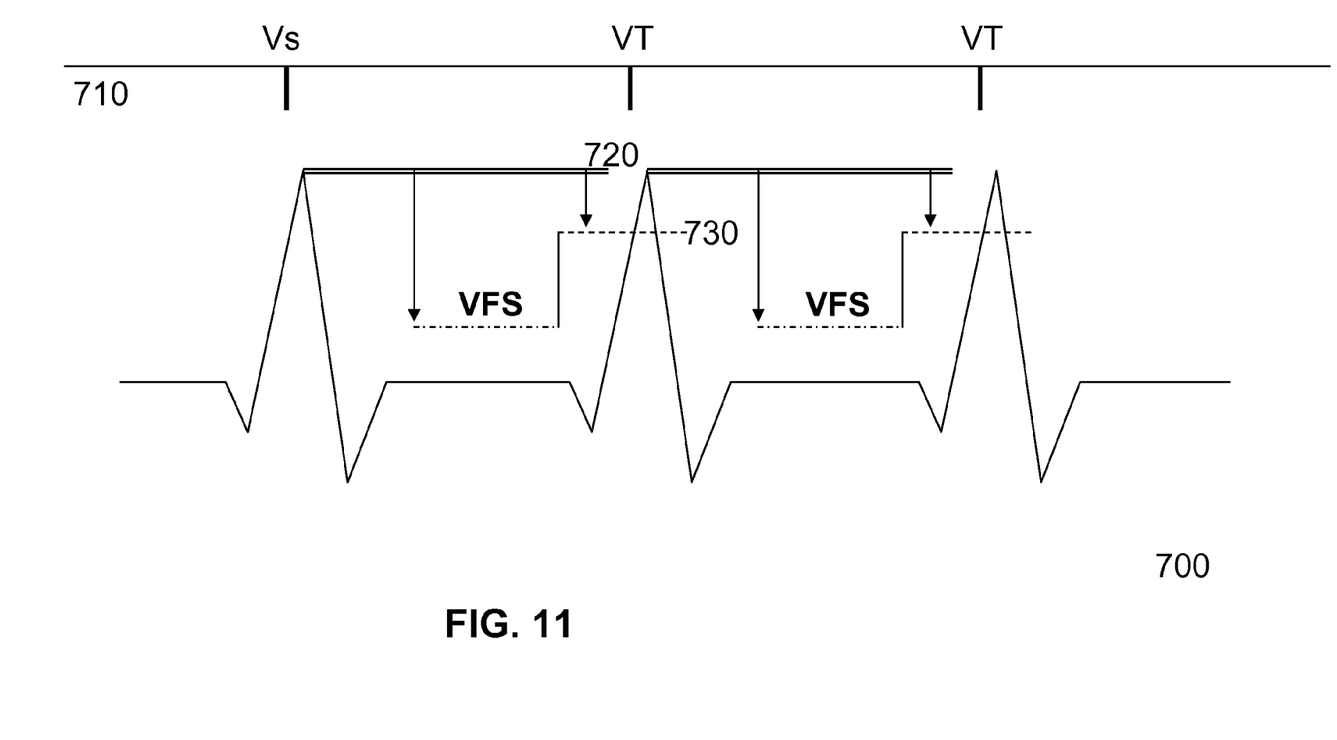
FIG. 11 shows an example of VF detection with a VF detection window (period)

FIG. 11 shows that the sensing of ventricular tachycardia (VT) takes place unchanged when a VF detection window (period) VFS is used. For a VT it can be assumed that the signal amplitudes fluctuate to a far less extent than for a ventricular fibrillation VF, and so the upper threshold 730, which was derived from the maximum amplitude 720, can be used here as the sensing criterion.

Figure 12:
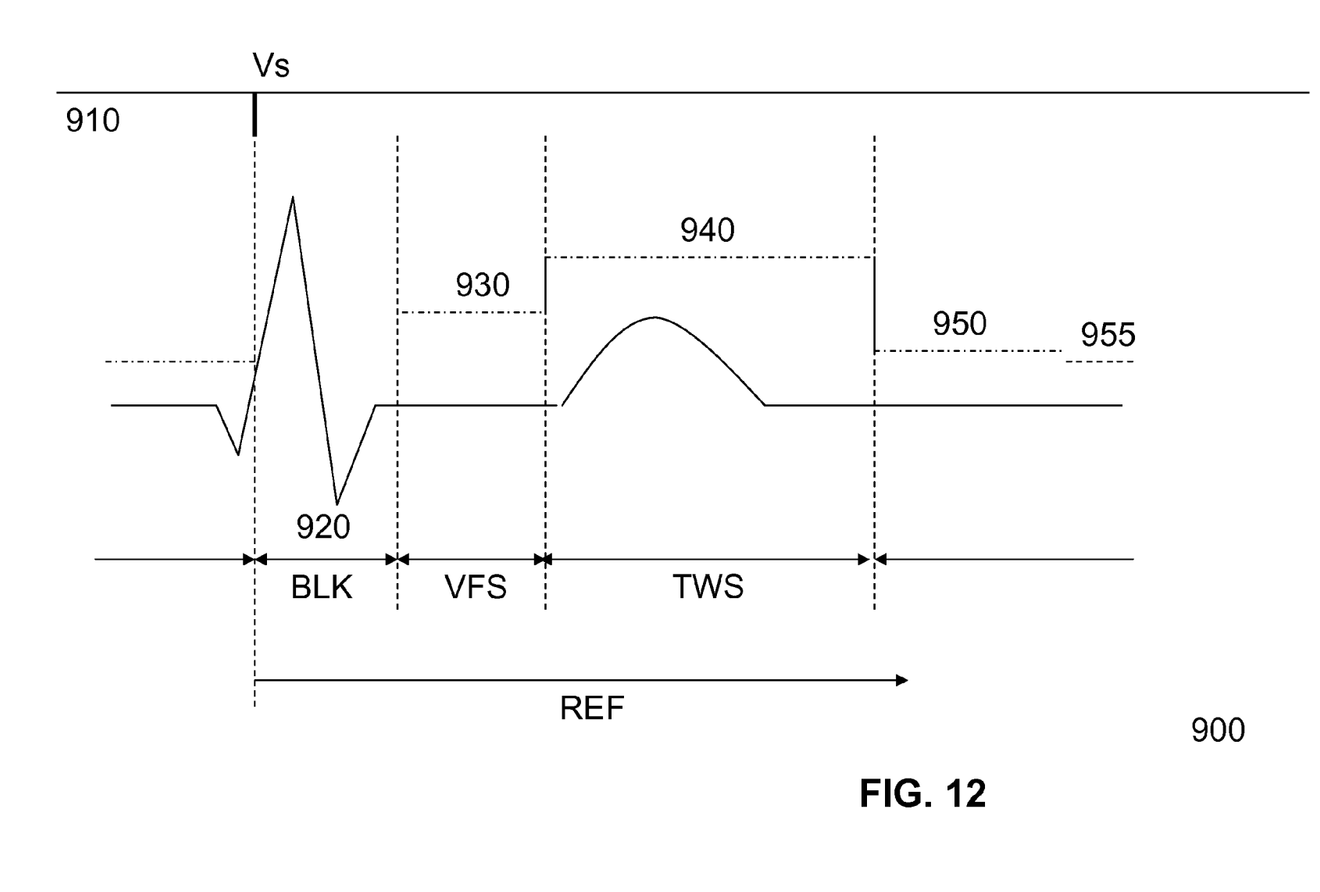
FIG. 12 shows typical timing with blanking and refractory periods.

FIG. 12 shows the ventricular sensing threshold control including a ventricular blanking period BLK, the VF detection window (period) VFS, a T wave blanking period TWS, and the refractory period (REF). When the sensing threshold is exceeded, a ventricular sense Vs is triggered in marker channel 910. A ventricular blanking period BLK 920 starts at this ventricular sense Vs to prevent multiple sensing within the QRS complex. During this period, no sensing that starts or resets the timer or the tachyarrhymia classification can be triggered, i.e., no further Vs can occur during BLK. When this blanking period BLK ends, sensing begins during the VF detection window VFS with VF detection threshold 930 in order to sense possible ventricular fibrillation with low amplitude. If none is present, once the adjustable VF detection window period VFS ends, the sensing threshold is raised to the T wave blanking value TWS 940 for the programmed T wave blanking period, and is then reduced to the so-called lower sensing threshold 950. This lower sensing threshold 950 can be reduced further, as usual, after defined time intervals (as seen at 955). All sensing thresholds can assume fixed values or values that are dependent on the maximum QRS signal amplitude.

The illustrated refractory period (REF) is started with the ventricular sense (Vs). Although a Vs that occurs within the refractory period is evaluated for the tachycardial rhythm assessment, it does not influence the pacemaker timer. The refractory period (REF) is independent of the control of the ventricular sensing thresholds.

The aforementioned arrangement improves the sensing of ventricular fibrillation in combination with high T wave suppression. It is therefore possible to develop automatic ICD systems that no longer require manual adjustment of the sensing parameters. This arrangement is also useful for unipolar ICD sensing electrodes, since the expression of the T wave and, mainly, the VF signal fluctuations are particularly critical here. The method can also be used with subcutaneously implanted ICD systems.

It will be apparent to those skilled in the art that numerous modifications and variations of the described examples and versions are possible in light of the foregoing discussion. The described examples and versions are presented for purposes of illustration only, and alternative versions may include some or all of the features disclosed herein. The invention is therefore not intended to be limited to the exemplary versions of the invention described above, but rather is intended to be limited only by the claims set out below. Thus, the invention encompasses all different versions that fall literally or equivalently within the scope of these claims.

What is claimed is:

1. An implantable cardiac stimulator including:
    a. a cardioversion/defibrillation unit:
        (1) connected or connectable to a ventricular sensing electrode and a ventricular defibrillation electrode, and
        (2) being configured to generate and deliver cardioversion shocks or defibrillation shocks,
    b. a ventricular sensing unit:
        (1) connected or connectable to the ventricular sensing electrode,
        (2) being configured to process a signal from the ventricular sensing electrode during each heart cycle to:
            (a) detect a chamber contraction,
            (b) thereafter detect, during a ventricular fibrillation detection period, whether the signal from the ventricular sensing electrode exceeds a first lower sensing threshold;
            (c) thereafter detect, during a T wave blanking period following the ventricular fibrillation detection period, whether the signal from the ventricular sensing electrode exceeds an upper sensing threshold greater than the first lower sensing threshold;
            (d) thereafter detect, following the T wave blanking period, whether the signal from the ventricular sensing electrode exceeds a second lower sensing threshold which is less than the upper sensing threshold.

2. The implantable cardiac stimulator of claim 1 wherein the first and the second lower thresholds are identical.

3. The implantable cardiac stimulator of claim 1 wherein the second lower threshold is less than or equal to the first lower threshold.

4. The implantable cardiac stimulator of claim 1 further including a control unit configured to adjust the duration of the ventricular fibrillation detection period depending on a measured heart rate.

5. The implantable cardiac stimulator of claim 4 wherein the control unit is configured to:
    a. start the T wave blanking period after a ventricular fibrillation detection period in which the first lower sensing threshold was not exceeded by the signal from the ventricular sensing electrode, and
    b. adjust the duration of the ventricular fibrillation detection period in dependence on the measured heart rate only if a T wave blanking period occurred in a preceding heart cycle.

6. The implantable cardiac stimulator of claim 1 wherein:
    a. the ventricular sensing electrode is defined by a pair of electrodes spaced on a lead,
    b. the ventricular sensing unit is configured to process a bipolar signal from the ventricular sensing electrode.

7. The implantable cardiac stimulator of claim 1 wherein:
    a. the ventricular sensing electrode is defined by:
        (1) an electrode on a lead, and
        (2) a housing about the ventricular sensing unit,
    b. the ventricular sensing unit is configured to process a unipolar signal from the ventricular sensing electrode.

8. The implantable cardiac stimulator of claim 7 wherein the ventricular sensing electrode is defined by:
    a. a coil extending along the a lead, and
    b. a housing about the ventricular sensing unit,
    wherein the ventricular sensing unit processes a far-field signal from the ventricular sensing electrode.

9. The implantable cardiac stimulator of claim 1 wherein:
    a. the ventricular sensing electrode is defined by electrodes on two or more leads, and
    b. the ventricular sensing unit is configured to process multiple vectors from the electrodes.

10. The implantable cardiac stimulator of claim 1 wherein the ventricular sensing unit is further configured to deliver a shock via the ventricular defibrillation electrode if the signal from the ventricular sensing electrode exceeds the first lower sensing threshold N times, where N is a predefined number greater than or equal to 1.

11. A method of detecting ventricular fibrillation with an implantable cardiac stimulator, wherein the implantable cardiac stimulator includes:
    A. a ventricular sensing electrode;
    B. a ventricular sensing unit connected or connectable to the ventricular sensing electrode, and
    C. a cardioversion/defibrillation unit configured to deliver a shock via a ventricular defibrillation electrode,
    wherein the method includes the steps of:
    a. detecting a chamber contraction within a signal from the ventricular sensing electrode during each heart cycle;
    b. thereafter detecting, during a ventricular fibrillation detection period, whether the signal from the ventricular sensing electrode exceeds a first lower sensing threshold;
    c. thereafter detecting, during a T wave blanking period following the ventricular fibrillation detection period, whether the signal from the ventricular sensing electrode exceeds an upper sensing threshold greater than the first lower sensing threshold;
    d. thereafter detecting, following the T wave blanking period, whether the signal from the ventricular sensing electrode exceeds a second lower sensing threshold which is less than the upper sensing threshold.

12. The method of claim 11 wherein the first and the second lower thresholds are identical.

13. The method of claim 11 wherein the second lower threshold is less than the first lower threshold.

14. The method of claim 11 further including the step of adjusting the duration of the ventricular fibrillation detection period in dependence on a measured heart rate.

15. The method of claim 14 wherein:
    a. the T wave blanking period is started after a ventricular fibrillation detection period in which the first lower sensing threshold was not exceeded by the signal from the ventricular sensing electrode, and b. the duration of the ventricular fibrillation detection period is adjusted in dependence on the measured heart rate only if a T wave blanking period occurred in a preceding heart cycle.

16. The method of claim 11 wherein the ventricular fibrillation detection period ends within 250 ms of the detected chamber contraction.

17. The method of claim 16 wherein the ventricular fibrillation detection period ends after 150 ms of the detected chamber contraction.

18. The method of claim 11 wherein the cardioversion/defibrillation unit delivers a shock if the signal from the ventricular sensing electrode exceeds the first lower sensing threshold during the ventricular fibrillation detection period.

19. The method of claim 18 wherein the cardioversion/defibrillation unit delivers a shock if the signal from the ventricular sensing electrode exceeds the first lower sensing threshold N times, where N is a predefined number greater than or equal to 1.

20. A method of detecting ventricular fibrillation with an implantable cardiac stimulator, wherein the implantable cardiac stimulator includes:
   A. a ventricular sensing unit configured to receive a signal from a ventricular sensing electrode, and
   B. a cardioversion/defibrillation unit configured to deliver a shock via a ventricular defibrillation electrode, wherein the method includes the steps of:
a. detecting a chamber contraction during each heart cycle;
b. thereafter detecting, during a ventricular fibrillation detection period which is less than the period of the preceding heart cycle, whether the signal from the ventricular sensing electrode exceeds a first lower sensing threshold;
c. if the signal from the ventricular sensing electrode exceeds the first lower sensing threshold:
   (1) repeating the foregoing step b.; and
   (2) delivering a shock via the ventricular defibrillation electrode if the signal from the ventricular sensing electrode exceeds the first lower sensing threshold N times, where N is a predefined number greater than or equal to 1;
d. if the signal from the ventricular sensing electrode does not exceed the first lower sensing threshold, thereafter detecting, during a T wave blanking period following the ventricular fibrillation detection period, whether the signal from the ventricular sensing electrode exceeds an upper sensing threshold greater than the first lower sensing threshold;
e. thereafter adjusting the duration of the ventricular fibrillation detection period in dependence on the period of at least one preceding heart cycle only if a T wave blanking period occurred in the immediately preceding heart cycle.

* * * * *